US009557314B2

(12) United States Patent
Jarvie et al.

(10) Patent No.: US 9,557,314 B2
(45) Date of Patent: Jan. 31, 2017

(54) APPARATUS AND METHOD FOR DETERMINING PHASE SEPARATION RISK OF A BLENDED FUEL IN A STORAGE TANK

(75) Inventors: Ian F. Jarvie, Woodridge, IL (US); Przemyslaw Olaf Iwaszczyszyn, La Grange, IL (US)

(73) Assignee: Delaware Capital Formation, Inc., Wilmington, DE (US)

( * ) Notice: Subject to any disclaimer, the term of this patent is extended or adjusted under 35 U.S.C. 154(b) by 1081 days.

(21) Appl. No.: 13/246,277

(22) Filed: Sep. 27, 2011

(65) Prior Publication Data
US 2012/0155504 A1    Jun. 21, 2012

Related U.S. Application Data

(60) Provisional application No. 61/388,199, filed on Sep. 30, 2010.

(51) Int. Cl.
*G01N 33/28* (2006.01)
*G01N 27/06* (2006.01)
*G01N 25/02* (2006.01)

(52) U.S. Cl.
CPC .......... *G01N 33/2852* (2013.01); *G01N 25/02* (2013.01); *G01N 27/06* (2013.01); *G01N 33/2811* (2013.01); *Y10T 137/8158* (2015.04)

(58) Field of Classification Search
CPC  G01N 33/2852; G01N 27/06; G01N 33/2811; Y10T 137/8158
USPC .............................. 137/551; 73/61.43, 61.59
See application file for complete search history.

(56) References Cited

U.S. PATENT DOCUMENTS

| 2,473,439 | A |   | 6/1949 | Maxfield |
| 3,457,772 | A |   | 7/1969 | Chassagne et al. |
| 4,539,107 | A |   | 9/1985 | Ayers |
| 4,579,097 | A | * | 4/1986 | Yamamoto et al. .......... 123/438 |
| 4,804,274 | A | * | 2/1989 | Green ............................ 374/17 |
| 6,540,797 | B1 |  | 4/2003 | Scott et al. |
| 7,645,070 | B2 | * | 1/2010 | Atwood et al. ............... 374/137 |
| 8,192,510 | B2 | * | 6/2012 | Mattingly et al. .............. 44/451 |

(Continued)

FOREIGN PATENT DOCUMENTS

| RU | 2113367 C1 | 6/1998 |
| RU | 2189026    | 9/2002 |

OTHER PUBLICATIONS

Jörg Baranski; International Search Report and Written Opinion issued in corresponding International Application No. PCT/US2011/053601; Feb. 29, 2012; 16 pages; European Patent Office.

(Continued)

*Primary Examiner* — Atif Chaudry
(74) *Attorney, Agent, or Firm* — Wood Herron & Evans LLP

(57) ABSTRACT

A method for improved handling of a blended fuel includes obtaining a sample of the blended fuel from a storage tank; cooling the same until the sample separates into phases; and determining a risk that the fuel in the storage tank will separate based on the cooling step. An apparatus for assessing the risk of phase separation of a blended fuel includes a test cavity for holding a sample of the blended fuel from a storage tank; a heat transfer device for cooling the sample in the test cavity; and at least one sensor for indicating when the sample in the test cavity has separated into phases.

38 Claims, 5 Drawing Sheets

(56) References Cited

U.S. PATENT DOCUMENTS

| | | | |
|---|---|---|---|
| 2005/0053116 A1 | 3/2005 | Tsang et al. | |
| 2006/0248952 A1 | 11/2006 | Jarvie | |
| 2008/0053202 A1* | 3/2008 | Rohklin et al. | 73/61.41 |
| 2010/0141949 A1* | 6/2010 | Bugge | 356/402 |
| 2010/0175313 A1 | 7/2010 | Mattingly et al. | |

OTHER PUBLICATIONS

International Bureau, International Preliminary Report on Patentability issued in corresponding PCT/US2011/053601 dated Apr. 11, 2013, 10 pages.

Zlata Muzikova et al; Volatility and Phase Stability of Petrol Blends with Ethanol; Fuel, IPC Science and Technology Press; Aug. 2009; pp. 1351-1356; Prague, Czech Republic.

Milan Lojkasek et al.: Solubility of Water in Blends of Gasoline, Methanol and a Solubilizer; Institute of Chemical Technology; Jan. 1992; pp. 113-123; Prague, Czechoslovakia.

Filiz Karaosmanoglu et al.; Effects of a New Blending Agent on Ethanol-Gasoline Fuels; Jan. 1996; pp. 816-820; Istanbul, Turkey.

Allan F. M. Barton et al.; Eucalyptus Oil as a Cosolvent in Water-Ethanol-Gasoline Mxtures; Jan. 1989; pp. 11-17; Perth, Western Australia.

F. Karaosmanoglu et al.; The Effects of Isopropanol Addition on Gasoline-Alcohol Motor Fuels Blends; Jan. 1988; pp. 125-128; Institute of Energy; London, Great Britain.

Federal Service for Intellectual Property, Official Action issued in Russian Application No. 2013120017/28(029620) dated Apr. 28, 2015.

Intellectual Property Office, Official Action issued in Taiwan Pat. Appln. No. 100135662 dated Jul. 28, 2015.

IP Australia, Patent Examination Report issued in Patent Application No. 2011307291 dated Feb. 28, 2014.

IP Australia, Patent Examination Report issued in Patent Application No. 2011307291 dated Nov. 20, 2014.

IP Australia, Patent Examination Report issued in Patent Application No. 2011307291 dated Jun. 27, 2014.

IP Australia, Patent Examination Report issued in Patent Application No. 2011307291 dated Mar. 5, 2015.

* cited by examiner

APPARATUS AND METHOD FOR DETERMINING PHASE SEPARATION RISK OF A BLENDED FUEL IN A STORAGE TANK

CROSS-REFERENCE TO RELATED APPLICATION

This application claims priority to U.S. Provisional Patent Application Ser. No. 61/388,199 filed Sep. 30, 2010, the disclosure of which is incorporated by reference herein in its entirety.

TECHNICAL FIELD

This invention relates to the separation of a fuel within a storage tank and, more particularly, to an apparatus and associated methods for determining the risk that a blended fuel within a storage tank will separate.

BACKGROUND

The impact of burning fossil fuels on the environment has been a well-documented problem and has garnered the attention of the international community. One of the major environmental problems confronting many of the countries of the world is atmospheric pollution caused by the emission of pollutants in the exhaust gases and gasoline vapor emissions from gasoline fueled automobiles. This problem is especially acute in major metropolitan areas where atmospheric conditions and the great number of automobiles result in aggravated conditions. While vehicle emissions have been reduced substantially, air quality still needs improvement. The result has been that regulations have been passed to further reduce such emissions by controlling the composition of fuels for automobiles and other motor vehicles. These specially formulated, low emission fuels are often referred to as reformulated or blended fuels and include, for example, various blended gasolines.

Governments and regulatory authorities throughout the world have focused on setting specifications for low emission blended gasoline. The specifications, however, require the presence of oxygenates in the gasoline. Oxygenated gasoline is a mixture of conventional hydrocarbon-based gasoline and one or more oxygenates. The current oxygenates used in blended gasolines belong to one of two classes of organic molecules: alcohols and ethers. More specifically, the primary oxygen-containing compounds employed in blended fuels today are methyl tertiary butyl ether (MTBE) and ethanol. While MTBE achieves its intended purpose of oxygenating the gasoline, the presence of ethers has begun to raise environmental concerns, such as contaminated ground and drinking water. Accordingly, more attention has recently been focused on ethanol oxygenated gasolines.

Ethanol fuel mixtures are a mixture of ethanol and gasoline and are designated with "E" numbers which describe the percentage of ethanol in the mixture by volume. A wide range of ethanol fuel mixtures are used throughout the world. For example, in the United States, E10 is most commonly used at gas stations. In this regard, E10 can be used in most conventional internal combustion engines without modification or redesign due to the usage of blended fuels. With the introduction of hybrid and other specially modified engines, higher percentages of ethanol have also been made available at selected gas stations. For example, E85 is also being sold at a number of locations throughout the United States. Other parts of the world also use ethanol blended fuels in varying percentages. For example, Brazil primarily uses E25 and many countries of Europe offer E5.

While the environmental benefits of ethanol blended fuels have been documented and the commercial usage has dramatically increased over the years, there remain practical challenges with these alternative fuels. In this regard, one problem with ethanol blended fuels is phase separation. Phase separation occurs when water is present to a minor, but nonetheless significant degree in the fuel. Such water may be introduced into the fuel by condensation of humid air in, for example, the ullage space of the storage tank, seepage of ground water into the storage tank, or possibly through other routes. Ethanol is hydrophilic and therefore has a high affinity for water such that when gasoline containing even small amounts of ethanol comes into contact with a sufficient amount of water (e.g., defined by a saturation point), the water will combine with the ethanol and come out of solution with the gasoline.

Although the ethanol will always combine with water, the ethanol and water will not come out of solution with the gasoline until the saturation point is reached. In any event, when phase separation occurs, stratification of the fuel within the storage tank takes place. In this regard, the water/ethanol mixture generally has a higher density as compared to the remaining gasoline and consequently, upon phase separation, the storage tank includes a lower layer of ethanol and water and an upper layer of gasoline (minus at least a portion of the ethanol of the original blend). The lower the ethanol content of the fuel, the more prone the fuel is to separation, as it takes a smaller amount of water to reach the saturation point of the blended fuel.

In a typical fuel dispensing system, such as gas stations and the like, the inlet to the submersible pump which supplies fuel to a dispensing unit is generally located near the lowermost portion of the storage tank. Thus, when phase separation of the blended fuel occurs, the inlet is typically located in the lower ethanol and water layer and the "fuel" that is supplied through the dispensing unit is not the desired blended fuel mixture. Accordingly, engines to which the dispensed fuel is being supplied may not operate properly.

When the blended fuel in the storage tank has separated, the gas station owner has few options for remedying the problem. In this regard, the conventional solution is to evacuate the storage tank and refill the tank with fresh blended fuel. This solution, however, is extremely costly. For example, the dispensing units that access fuel from the separated tank must be shut down so that customers are not able to dispense potentially defective fuel from those units. These shutdowns result in decreased sales and increased consumer dissatisfaction. Additionally, the phase separated fuel is considered a hazardous waste by the EPA and other authorities and must be removed from the tank and transported back to a refinery for reprocessing. Such a process is not only costly, but is time consuming as well.

Various devices have been developed to indicate when phase separation of a blended fuel in the storage tank has occurred. These devices, however, are typically binary type output devices in that they only indicate phase separation or no phase separation (either the fuel is separated or it is not). So long as such a device does not indicate that the fuel has separated, fuel may be supplied to the dispensing units for use by the consumer. Of course once the device indicates that phase separation of the fuel in the storage tank has occurred, the appropriate pumps and dispensing units may be disabled so that the potentially defective fuel is not dispensed to a customer.

While generally being effective for indicating whether phase separation has or has not occurred, such devices do not provide any predictive capabilities, i.e., indicating a risk of phase separation before phase separation actually occurs. In other words, a device that simply indicates whether phase separation has or has not occurred provides minimal value to gas station owners. In this regard, once phase separation of the blended fuel has occurred, it is too late for the gas station owner to take steps that might mitigate or prevent the impending separation, or allow the owner to minimize any potential financial losses caused by the fuel separating into its various phases. As far as the gas station owner is concerned, the only action left to be taken is to remove the separated fuel from the storage tank and refill the tank with fresh blended fuel. Thus, the aforementioned devices do not help the owner mitigate or avoid the high costs associated with the removal and replenishment of fuel when phase separation occurs.

Consequently, there is a need for an improved device and associate methods that can assess, predict or otherwise provide an indication as to the risk of phase separation of a blended fuel in a storage tank prior to the fuel actually separating.

SUMMARY

A method for improved handling of a blended fuel includes obtaining a sample of the blended fuel from a storage tank; cooling the same until the sample separates into phases; and determining a risk that the fuel in the storage tank will separate based on the cooling step. In one embodiment, obtaining the same of blended fuel includes initiating the flow of fuel into a test cavity, and stopping the flow of fuel when a sufficient amount of blended fuel is disposed in the test cavity. Additionally, this may include opening an inlet control value controlling the flow of fuel into the test cavity, and closing an exit control valve for controlling the flow of fuel out of the test cavity.

In one embodiment, cooling the sample includes activating a heat transfer device configured to remove heat from the sample. This may be achieved, for example, by applying an electrical signal to a thermoelectric device, such as a Peltier device. Heat may then be removed from the heat transfer device. In one embodiment, removing heat from the heat transfer device may include circulating fuel so as to remove heat from the heat transfer device. For example, this may be achieved by circulating fuel through a heat sink cavity in thermal communication with the heat transfer device.

The method may further include determining whether the fuel in the storage tank has separated prior to cooling the sample. In one embodiment, this may include measuring a fluid property of the sample, and comparing the measured fluid property to a value of the fluid property corresponding to the unseparated blended fuel. Based on this comparison, the method may include concluding that the fuel in the storage tank has not separated when the difference between the measured value and the value of the blended fuel is less than a threshold value. Alternatively, it may be concluded that the fuel in the storage tank has separated when the difference is greater than the threshold value. An alternative approach to determining whether the fuel in the storage tank has separated prior to cooling the sample includes measuring a fluid property of the fuel in the storage tank, and comparing the measured fluid property to a value of the fluid property corresponding to the unseparated blended fuel. Again, based on this comparison, the method may include concluding that the fuel in the storage tank has not separated when the difference between the measured value and the value of the blended fuel is less than a threshold value. Alternatively, it may be concluded that the fuel in the storage tank has separated when the difference is greater than the threshold value.

The method may further include determining whether the sample has separated during the time in which the sample is being cooled. The determining step may be done continuously or at discrete time steps. In one embodiment, this determining step may include measuring a fluid property of the sample at a first location; measuring the fluid property of the sample at a second location; and comparing the measured fluid property values. Based on this comparison, the method may include concluding that the sample has not separated when the difference between the measured values is less than a threshold value, or alternatively, concluding that the sample has separated when the difference is greater than the threshold value.

In one embodiment, the method includes determining the temperature of the fuel in the storage tank, such as an initial temperature prior to cooling the sample. The method may further include determining the temperature of the sample when the sample separates into its phases. In one embodiment, determining the risk that the fuel in the storage tank will separate may include defining a risk factor. In an exemplary embodiment, the risk factor may be defined by a difference between the temperature of the fuel in the storage tank and the temperature of the sample when the sample separates. When the risk of phase separation reaches a threshold criteria, the method may include sending an alert to an operator.

In one aspect of the invention, the method may include determining the water content of the fuel in the storage tank. This may be achieved, for example, by determining the temperature of the sample when the sample separates, and determining the water content of the sample using the saturation temperature. In an exemplary embodiment, determining the water content using the saturation temperature includes using a look up table that provides saturation curve information.

In addition to determining the risk of phase separation to the gas station owner, in accordance with a further embodiment of the method, the risk of phase separation to the customer may also be determined. This aspect of the method may include determining the temperature of the sample when the sample separates; determining an environmental temperature; and defining a risk factor by a difference between the environmental temperature and the temperature of the sample when the sample separates.

In another embodiment, a method for improved handling of a blended fuel includes obtaining a sample of the blended fuel from a storage tank; determining whether the fuel in the storage tank has separated; determining the temperature of the fuel in the storage tank; cooling the sample until the sample separates into phases; determining whether the sample has separated as the sample is being cooled; determining the temperature of the sample when the sample separates; and determining a risk that the fuel in the storage tank will separate based on a difference between the temperature of the fuel in the storage tank and the temperature of the sample when it separates.

An apparatus for assessing the risk of phase separation of a blended fuel includes a test cavity for holding a sample of the blended fuel from a storage tank; a heat transfer device for cooling the sample in the test cavity; and at least one sensor for indicating when the sample in the test cavity has separated into phases. For example, the at least one sensor may include an electrical conductivity sensor. In one embodiment, a sensor may be located adjacent a top of the test cavity and a sensor may be located adjacent a bottom of the test cavity. The apparatus may further comprise a temperature sensor that is associated with the test cavity. Additionally, the apparatus may include a heat sink cavity for removing heat from the heat transfer device and a temperature sensor associated with the heat sink cavity. A controller may be included which is operatively coupled to the test cavity and the heat transfer device.

In a further embodiment a fuel dispensing system includes a storage tank containing a blended fuel; a dispensing unit configured to dispense the blended fuel; a conduit line between the storage tank and the dispensing unit for transporting the fuel; and a phase separation monitoring device for providing information about the fuel in the storage tank relative to separation of the fuel.

BRIEF DESCRIPTION OF THE DRAWINGS

The accompanying drawings, which are incorporated in and constitute a part of this specification, illustrate embodiments of the invention and, together with a general description given above, and the detailed description given below, serve to explain various aspects of the invention.

DETAILED DESCRIPTION

Figure 1:
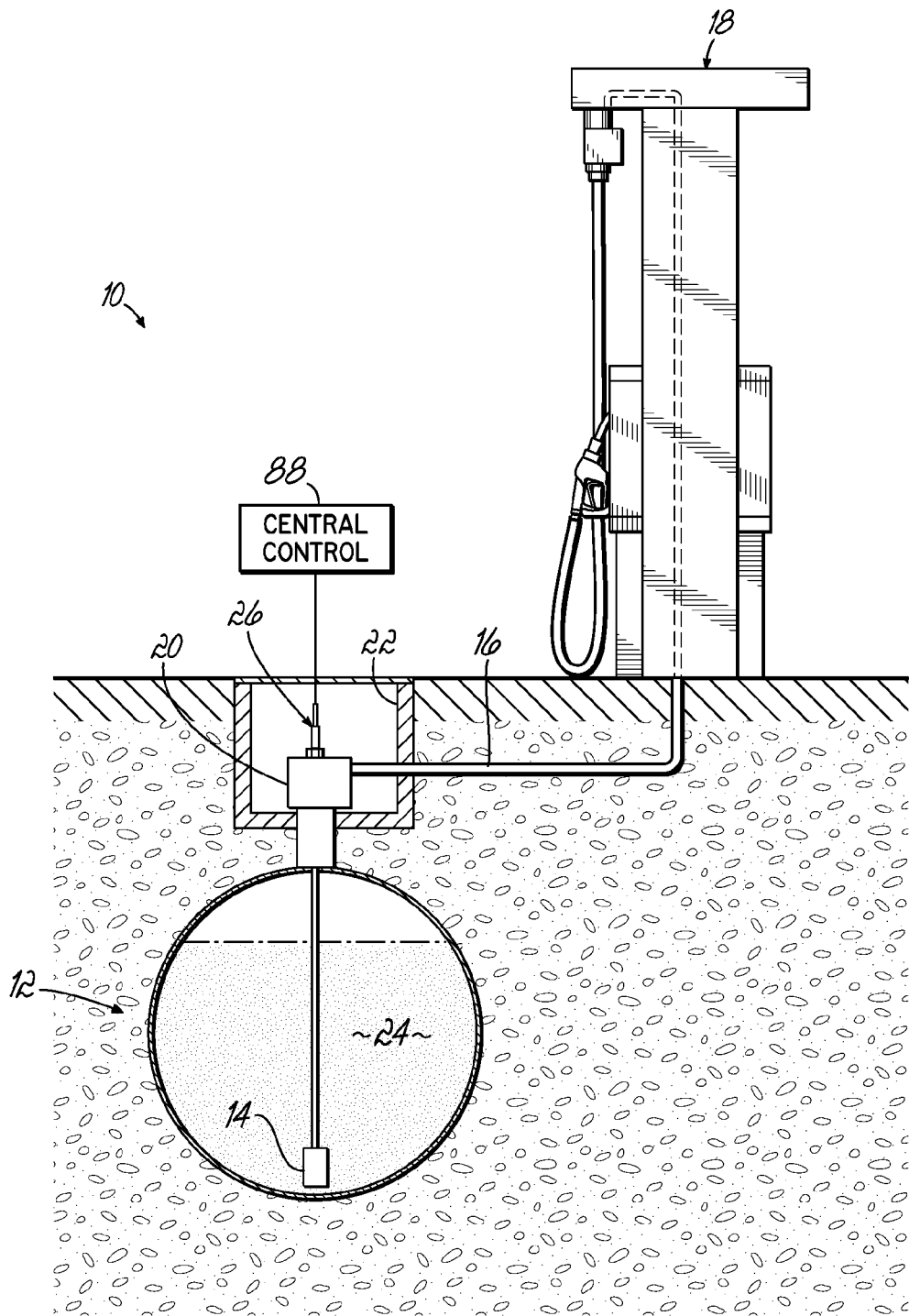
FIG. 1 is a diagrammatic illustration of an exemplary fuel dispensing system including a phase separation device in accordance with an embodiment of the invention.

An exemplary fuel dispensing system 10 in accordance with embodiments of the invention is shown in FIG. 1 and generally includes an underground storage tank ("UST") 12 for storing a fuel, a submersible pump 14 located in the tank 12, and a fluid conduit line 16 that transports the fuel under pressure to one or more dispensing units 18. Typically, the fluid conduit line 16 is coupled to the submersible pump 14 via a pump manifold 20 that is typically located external to tank 12, such as in an accessible covered manway 22. The storage tank 12 is configured to hold a supply of a reformulated or blended fuel. More particularly, the storage tank 12 is configured to hold an ethanol blended gasoline, such as, for example and without limitation, E10 or E85 and shown schematically as 24 in FIG. 1. It should be recognized, however, that other blended fuels susceptible to phase separation may also benefit from aspects of the invention.

As noted above, the blended fuel 24 is susceptible to phase separation when a sufficient amount of water is introduced into the storage tank 12. As also noted above, it is desirable to provide a device that can provide an indication of risk as to an impending phase separation of the fuel 24 in the storage tank 12. To this end, and in an advantageous aspect of the invention, the fuel dispensing system 10 includes a phase separation monitoring device, shown schematically at 26, configured to indicate how close the blended fuel 24 is to its saturation point and separating into its water/ethanol phase (lower layer) and gasoline phase (upper layer). Because phase separation device 26 is predictive, in the sense that it provides the risk or chances that separation is going to occur prior to it actually occurring, the gas station owner may initiate prophylactic measures that delay or prevent the onset of phase separation, take measures that minimize financial losses, attempt to identify the source of the leak, and/or take other actions that were not previously available using existing devices.

Figure 2:
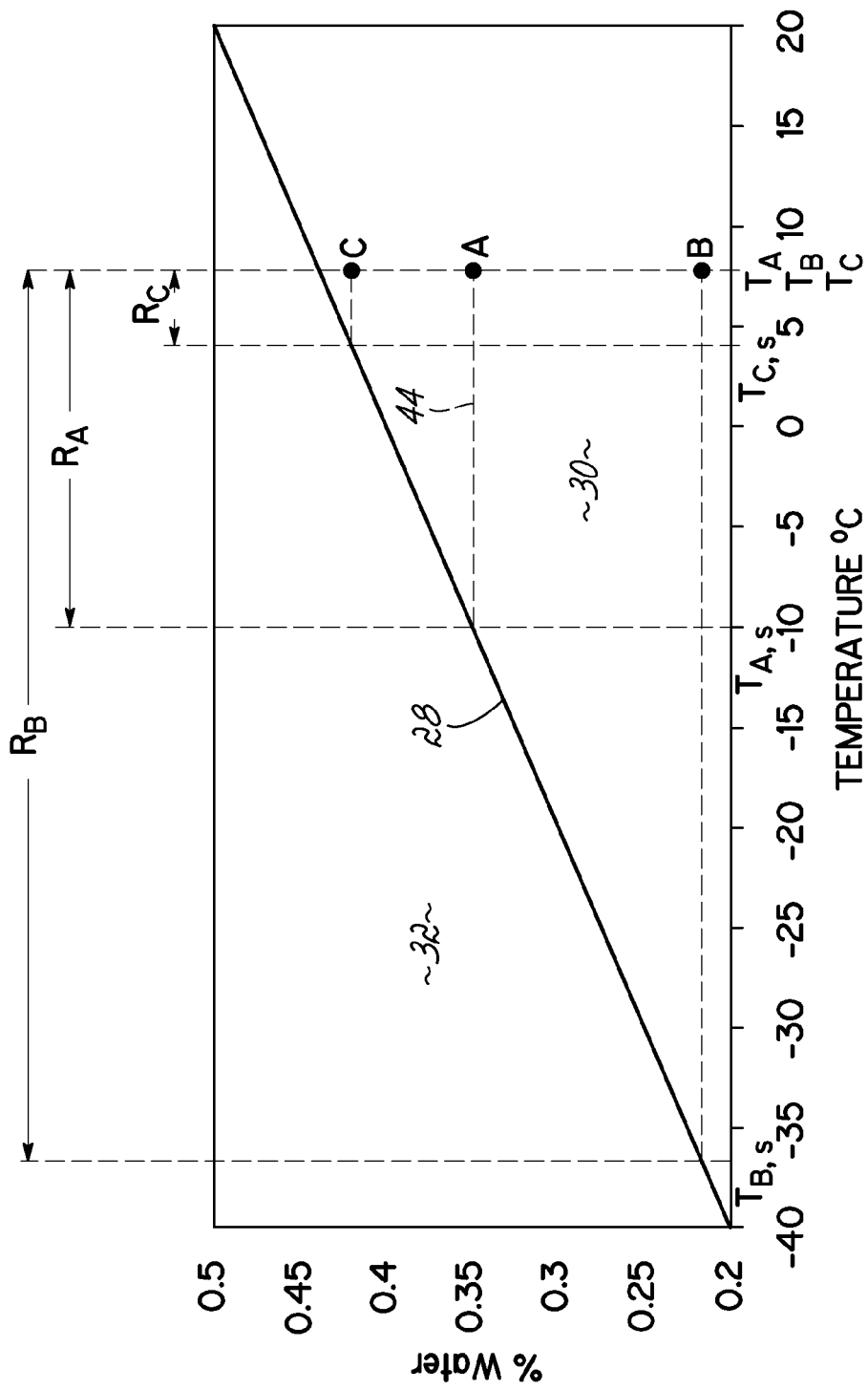
FIG. 2 is a schematic illustration of a saturation curve for a blended fuel.

Before delving into a detailed description of the phase separation device 26, it is considered instructive to discuss the theory on which the phase separation device 26 operates. In this regard, it is generally recognized that the saturation curve (i.e., the percentage of water required for the fuel to separate) of an ethanol blended gasoline is temperature dependent. To this end, FIG. 2 is a schematic illustration showing a characteristic saturation curve 28 for an ethanol blended gasoline. The saturation curve 28 defines a lower region 30 wherein the ethanol remains in solution with the gasoline and there is no phase separation of the fuel, and an upper region 32 wherein phase separation has occurred. It is understood that the saturation curve 28 for a particular ethanol blend (e.g., E10) may be readily determined by one of ordinary skill in the art.

Figure 3:
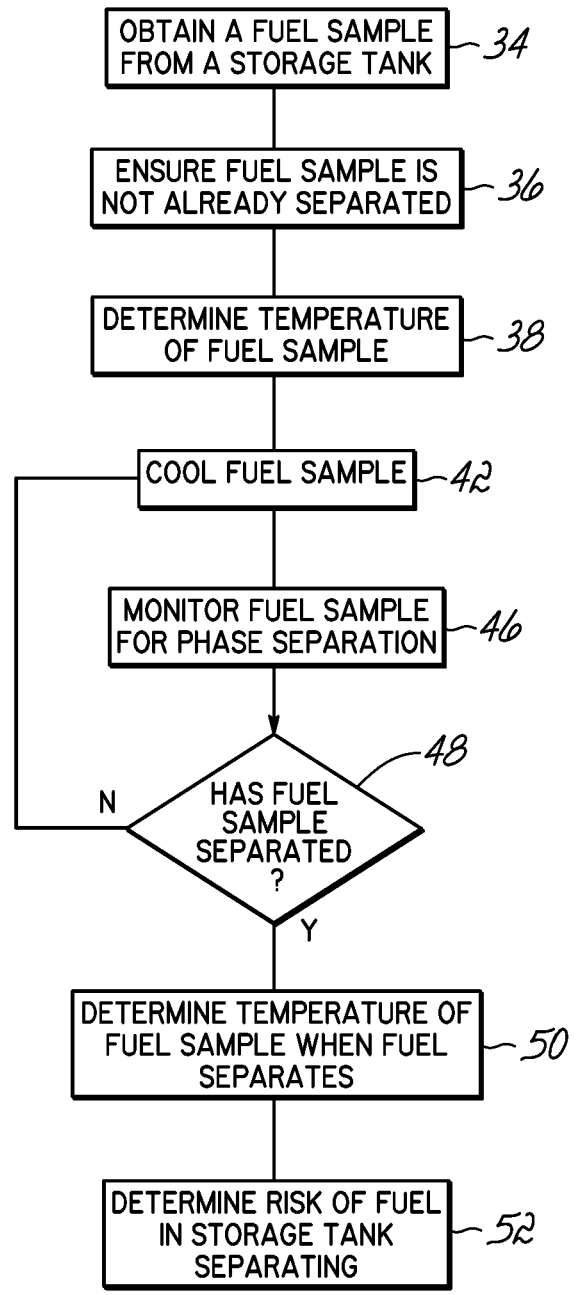
FIG. 3 is a flow chart illustrating an exemplary methodology for determining the risk that a blended fuel in a storage tank will separate.

Keeping this general relationship in mind, an exemplary methodology demonstrating the operation of separation device 26 is provided in FIG. 3 and explained pictorially in reference to FIG. 2. In accordance with an embodiment of the inventive method, a fuel sample, for illustrative purposes referred to herein as Sample A, is obtained from the storage tank 12 containing the ethanol blended gasoline, as indicated in step 34. Either prior to obtaining the fuel sample or subsequent to obtaining the fuel sample, an operator must ensure that the fuel sample has not been obtained from an already separated fuel tank, as indicated in step 36. In other words, it must be established that the fuel sample has the ethanol in solution with the gasoline and phase separation has not already occurred. It is recognized that such a fuel sample would be below the saturation curve 28 and in lower region 30 and is schematically indicated on FIG. 2 as point A. Next, the initial temperature of the fuel sample, which corresponds to the temperature of the fuel 24 in storage tank 12, is determined, as in step 38. For purposes of discussion, this temperature is indicated in FIG. 2 as $T_A$.

Following this step, the fuel sample is cooled so as to lower its temperature, as indicated in step 42. It should be noted that the percentage of water in the fuel sample remains fixed such that during the cooling step, the state of the fuel travels along a path identified by horizontal line 44 in FIG. 2. As the fuel sample is being cooled, the sample is being monitored for separation of the fuel into its various phases, as indicated in step 46. As indicated in step 48, if the fuel sample has not separated, then cooling of the fuel sample is continued. If, on the other hand, the fuel separates into its various phases, then the temperature of the fuel sample at its saturation point (i.e., the temperature at which the fuel separates) is determined, as at step 50. This saturation temperature is noted in FIG. 2 as $T_{A,s}$.

With the saturation temperature $T_{A,s}$ known, a risk factor R can be defined which correlates to how close the blended fuel 24 in the storage tank 12 is to its separation point, as indicated in step 52. By way of example and not limitation, the risk factor R can be defined as the difference between the initial temperature of the fuel sample $T_A$ (which corresponds to the temperature of the fuel in the tank) and the saturation temperature of the fuel sample $T_{A,s}$. In equation form, an indication of the risk of phase separation may be defined by $R_A=T_A-T_{A,s}$. Of course when defining risk in this manner, the larger the risk factor, the lower the risk that the fuel 24 in the storage tank 12 will separate, and the smaller the risk factor, the higher the risk that the fuel 24 in the storage tank 12 will separate. While this equation provides one metric for assessing phase separation risk of the blended fuel 24 in the storage tank 12, it should be recognized that other metrics may be defined which correspond in some manner to a phase separation risk and the invention is not limited to the particular metric used herein. For example, the risk factor may be defined in such a manner that the larger the risk factor, the higher the risk that the fuel in the storage tank will separate and vice versa. Additionally or alternatively, the risk factor may be normalized so as to be between zero and one, for example.

For purposes of comparison, FIG. 2 includes a schematic illustration of two additional fuel samples, Sample B and Sample C, that are acted on in accordance with the methodology of FIG. 3. In this schematic illustration, Sample B has an initial temperature of $T_B$ (same as $T_A$), a saturation temperature of $T_{B,s}$, and thus a risk factor of $R_B=T_B-T_{B,s}$. As illustrated in FIG. 2, the risk factor $R_B$ is greater than risk factor $R_A$, indicating that the fuel in Sample B has a decreased risk of separating. In contrast, Sample C has an initial temperature of $T_C$ (same as $T_A$ and $T_B$), a saturation temperature of $T_{C,s}$, and thus a risk factor of $R_C=T_C-T_{C,s}$. As illustrated in FIG. 2, the risk factor $R_C$ is less than risk factor $R_A$, indicating that the fuel in Sample C has an increased risk of separating. Based upon that shown in FIG. 2, it can be appreciated that $R_B>R_A>R_C$, thus Sample B is "safer" than Sample A, which is "safer" than Sample C.

Figure 4:
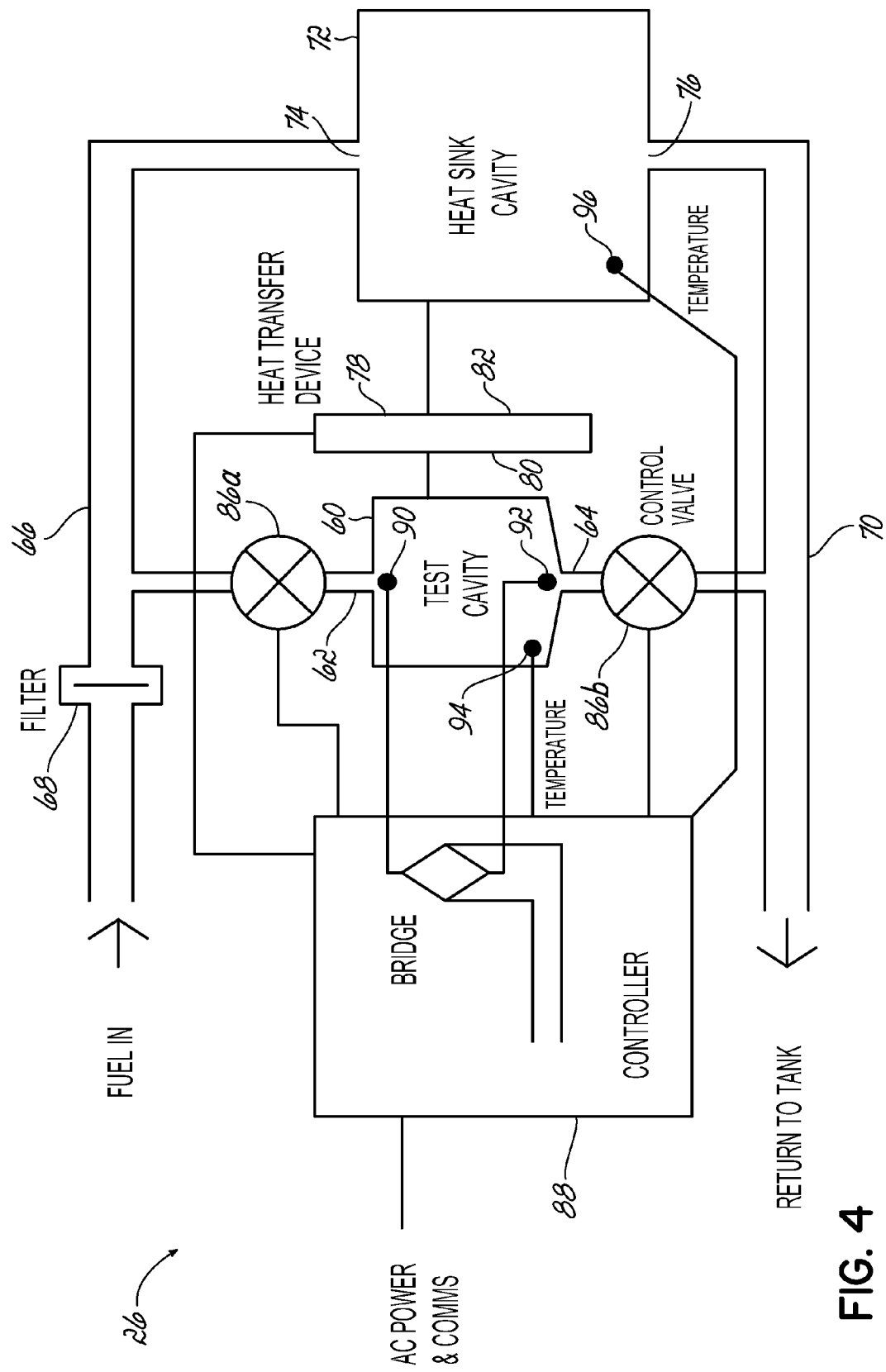
FIG. 4 is a diagrammatic illustration of an apparatus for carrying out the methodology of FIG. 3.

A schematic of a phase separation device 26 capable of carrying out the methodology described above is shown in FIG. 4. The phase separation device 26 includes a test cavity 60 having an inlet 62 and an exit 64. The inlet 62 is in fluid communication with a feed conduit 66, which is in turn in fluid communication with the storage tank 12 and configured to supply fuel from the storage tank 12 to the test cavity 60. The feed conduit 66 may include one or more filters 68 upstream of the inlet 62. Similarly, the exit 64 of test cavity 60 is in fluid communication with a return conduit 70, which is in turn in fluid communication with the storage tank 12 and configured to return fuel to the storage tank 12.

In one embodiment, a heat sink cavity 72 is in parallel relation to the test cavity 60 between the feed conduit 66 and the return conduit 70. In this regard, the heat sink cavity 72 includes an inlet 74 in fluid communication with feed conduit 66 and an exit 76 in fluid communication with return conduit 70. The feed conduit 66 and the return conduit 70 may be coupled through the heat sink cavity 72 such that the feed conduit 66, heat sink cavity 72, and the return conduit 70 form a loop with the storage tank 12. The purpose of this loop will be described in more detail below. It should be recognized that although the test cavity 60 and heat sink cavity 72 are shown and described as being in parallel relation relative to feed and return conduits 66, 70, the invention is not so limited. For example, the flow of fuel through the heat sink cavity 72 may be via a conduit in fluid communication with the storage tank 12 that is completely separate from feed conduit 66 (e.g., a totally separate loop, not shown). Thus, other flow arrangements to test cavity 60 and heat sink cavity 72 are contemplated to be within the scope of the present invention.

A heat transfer device 78 is thermally disposed between the test cavity 60 and the heat sink cavity 72. In this regard, the heat transfer device 78 includes a first portion 80 in thermal communication with the test cavity 60 and configured to extract heat from the test cavity 60, and more particularly, extract heat from the fuel sample in the test cavity 60. In one embodiment, the test cavity 60 may be thermally insulated but for its interface with the heat transfer device 78. This may provide, for example, increased control over the cooling process and allow accurate results from even small volume fuel samples. The heat transfer device 78 also includes a second portion 82 in thermal communication with the heat sink cavity 72 and configured to deliver heat to the heat sink cavity 72, and more particularly, deliver heat to the fuel flowing through the heat sink cavity 72. In one embodiment, the heat transfer device 78 may include a thermoelectric device, such as a Peltier device. It should be recognized, however, that other heat transfer devices may be used in various embodiments of the invention and embodiments of the invention are not limited to the Peltier device shown herein. Peltier devices are generally well known in the art and commercially available. Thus, a detailed description of their structure and operation is deemed unnecessary for a full understanding of the present invention.

The phase separation device 26 may further include one or more control valves 86 capable of controlling the flow of fuel into and/or out of the test cavity 60. By way of example and without limitation, a control valve 86a may be associated with the inlet 62 to the test cavity 60 and a control valve 86b may be associated with the exit 64 of the test cavity 60. Although not shown, additional control valves may be located in the feed conduit 66, the return conduit 70, the heat sink cavity 72, or a combination thereof. These values may be used to control the flow of fuel through the heat sink cavity 72.

The phase separation device 26 may be coupled to a controller, shown schematically at 88, to facilitate operation of the phase separation device 26, as discussed in more detail below. In one embodiment, the controller 88 may be a local controller (i.e., located on or adjacent the phase separation device 26 and dedicated to primarily operating the phase separation device 26) configured to communicate with other separate controllers that operate the fuel dispensing system 10. Alternatively, the controller 88 may form part of a larger control system (e.g., a central control) for operating the fuel dispensing system 10, as illustrated in FIG. 1. In any event, the controller 88 is operatively coupled to the phase separation device 26 and, in conjunction therewith, is capable of carrying out the methodology discussed above.

In this regard, the controller 88 may be operatively coupled to the test cavity 60. More particularly, the controller may be coupled to a first sensor 90 located adjacent a top of the test cavity 60 (e.g., relative to a gravitational field) and a second sensor 92 adjacent a bottom of the test cavity 60. The first and second sensors 90, 92 are configured to measure a fluid property of the fuel sample in the test cavity 60 at its top and bottom, respectively, in order to determine whether the fuel has separated into its phases. The fluid property measured by the first and second sensors 90, 92 may be judiciously selected such that when the fuel separates the measurements from the sensors 90, 92 are sufficiently different that a reasonable conclusion may be drawn that the fuel in the test cavity 60 has separated.

By way of example and without limitation, the sensors 90, 92 may be configured to measure the electrical conductivity of the fluid adjacent the sensors 90, 92. In this regard, it is known, for example, that the conductivity of gasoline is relatively low and the conductivity of ethanol and water is relatively high. Accordingly, when the difference in the sensor measurements is significant, it may be reasonable to conclude that the fuel sample in the test cavity 60 has separated. It should be recognized that aspects of the invention are not limited to the sensors 90, 92 measuring the electrical conductivity of the fuel, as there may be other fluid properties which can be measured and used to indicate phase separation of a blended fuel.

In addition to the above, the controller 88 may be operatively coupled to a temperature sensor 94 located on, in or in close proximity to the test cavity 60 and configured to measure the temperature of the fuel therein. The temperature sensor 94 may be any of the wide variety of temperature sensors generally known in the art and commercially available. These include, without limitation, thermocouples, thermistors, RTDs, etc.

The controller 88 may also be operatively coupled to heat sink cavity 72. More particularly, the controller 88 is operatively coupled to a temperature sensor 96 located on, in or in close proximity to the heat sink cavity 72 and configured to measure the temperature of the fuel flowing therethrough. The temperature sensor 96 may be any of the wide variety of temperature sensors generally known in the art and commercially available, including, without limitation, thermocouples, thermistors, RTDs, etc. The size of the heat sink cavity 72 and the flow rate of fuel flowing therethrough is configured such that the temperature of the fuel does not significantly change during operation. In other words, although the fuel flowing through the heat sink cavity 72 is accepting heat from the heat transfer device 78 (which in turn is being drawn from the test cavity 60), the temperature of the fuel does not appreciably change. At a minimum, the heat absorbed by the fuel does not change the temperature of the fuel 24 in the storage tank 12. In this way, the reading from temperature sensor 96 provides a reasonably accurate temperature of the fuel in the storage tank 12.

The controller 88 is further operatively coupled to the control valves 86 for moving the control valves 86 between their opened and closed positions. Furthermore, the controller 88 is operatively coupled to the heat transfer device 78 for controlling the cooling of the fuel sample in the test cavity 60 (e.g., control the cooling rate).

Figure 5:
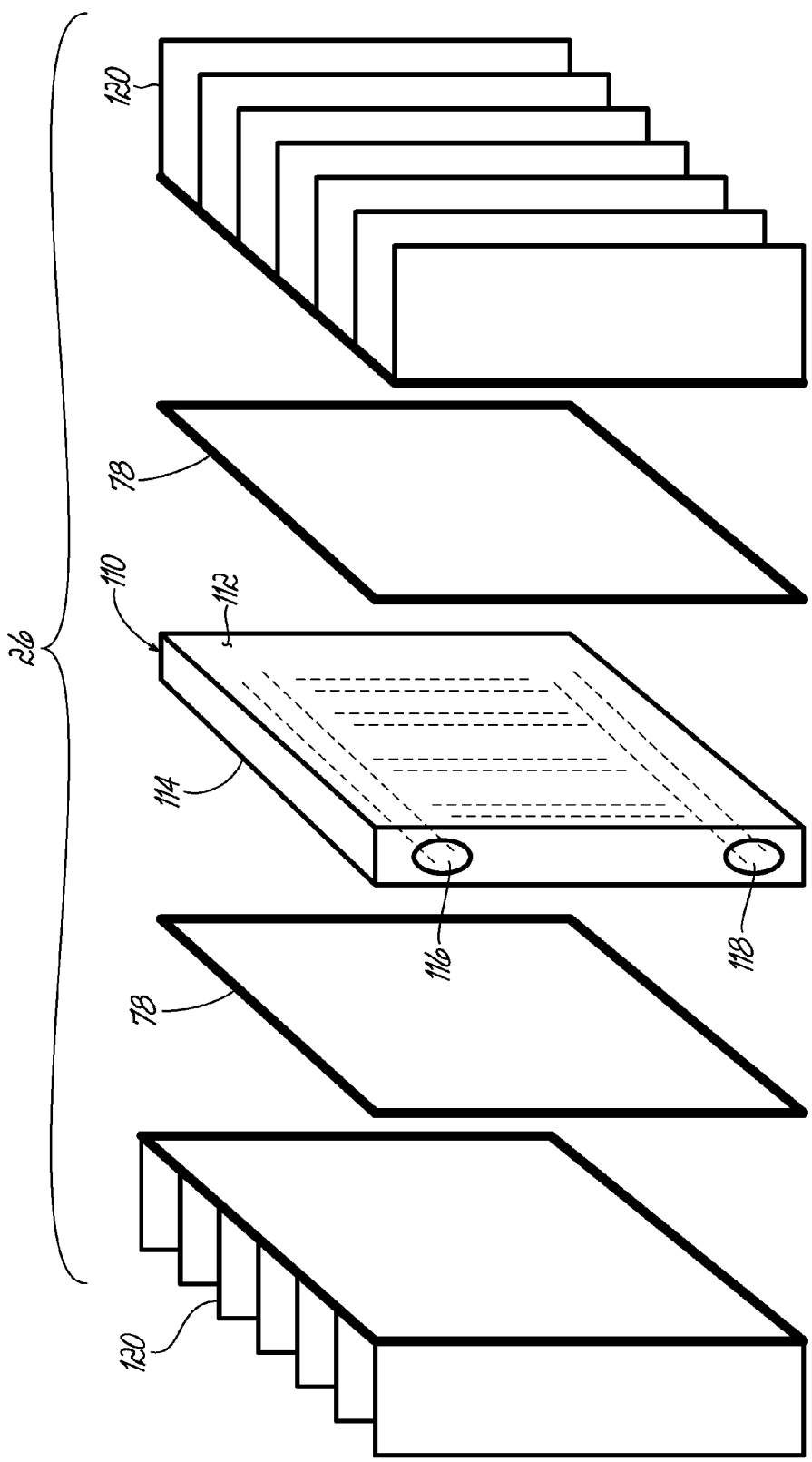
FIG. 5 is a partial disassembled perspective view of an apparatus in accordance with one embodiment of the invention for carrying out the methodology of FIG. 3.

An exemplary phase separation device 26 is shown in FIG. 5. The phase separation device 26 includes a plate-like housing 110 having first and second opposed surfaces 112, 114. The housing 110 also includes an inlet 116, an exit 118, and control valves and conduits (not shown) to allow fuel to flow to the test cavity 60 inside the housing 110 (not shown). Heat transfer devices 78, such as Peltier devices, are thermally coupled to the surfaces 112, 114 for removing heat from the test chamber 60. Finned heat exchangers 120 are coupled to the heat transfer devices 78 to facilitate the removal of heat. In this regard and as discussed above, fuel 24 from the storage tank 12 flows over the finned heat exchangers 120 to remove the heat from the heat transfer device 78 and thereby allow further cooling of the fuel sample in the test cavity 60. Although exemplary embodiments describe removing heat from the heat transfer device 78 essentially using the fuel as a coolant, it should be recognized that the heat may be removed from the heat transfer device(s) 78 through alternative means. For example, one or more fans may be used to remove heat from the heat transfer device(s) 78. Further alternatively, water or some other coolant may flow over the finned heat exchanger 120 to remove the heat. Accordingly, the invention should not be limited to using fuel to remove the heat from the heat transfer device(s) 78.

Operation of an exemplary phase separation device 26 will now be described in further detail. For purpose of discussion, operation will be described in reference to the schematic illustrated in FIG. 4. When it is desired to conduct a test on the fuel 24 in the storage tank 12, the controller 88 may activate the control valves 86 so as to provide a fuel sample for testing. In this regard, the controller 88 may activate control valve 86a so as to move the valve 86a to the opened position, and activate control valve 86b so as to move the valve 86b to the closed position such that fuel is capable of flowing into and being retained within test cavity 60. When a suitable amount of fuel has entered the test cavity 60, the controller 88 may activate control valve 86a so as to move the valve 86a to its closed position and thereby isolate a fuel sample within the test cavity 60.

Prior to cooling the fuel sample, a check must be performed to ensure that the fuel sample was not obtained from a storage tank 12 that was already separated such that, for example, the fuel sample in the test cavity 60 is substantially ethanol and water and not the desired blended fuel with the ethanol in solution with the gasoline. In one embodiment, this may be done, for example, by analyzing the measurements from first and second sensors 90, 92. In this regard, the controller 88 may include one or more microprocessors or other hardware, circuitry, etc. capable of analyzing the signals received from first and second sensors 90, 92. In the instant case, it should be understood that a difference in measurements between the first and second sensors 90, 92 is not necessarily determinative that the fuel sample is the desired blended fuel and not an already separated phase thereof. For example, if the fuel sample in test cavity 60 is ethanol and water, then the measurements from sensors 90, 92 would presumably be about the same, thereby providing substantially no difference in measurements. This might falsely lead one to believe that the fuel sample has not separated (because there is no difference in measurements), when in fact the fuel sample is one of its separated phases.

Thus, to ensure that the fuel sample is the desired blended fuel and not a separated phase thereof, the magnitudes of the measurements from sensors 90, 92 may be examined. In this regard, the measurements from sensors 90, 92 should correspond to the value of the fluid property (e.g., electrical conductivity) for the desired blended fuel. If the magnitude of the measurements is relatively high, then the fuel sample may be ethanol and water, indicating that the fuel in the storage tank 12 has already separated. Similarly, if the magnitude of the measurements is relatively low, then the fuel sample may be gasoline (without the desired amount of ethanol), again indicating that the fuel in the storage tank 12 has already separated.

The controller 88 may include a memory or other information storage device for storing a nominal value of the fluid property of the blended fuel being measured by the sensors 90, 92. If the measured values are relatively close to the stored value (e.g., +/−15%), then it may be reasonably concluded that the fuel 24 in the storage tank 12 has not separated and the controller 88 may be configured to continue with the test of the fuel sample. If not, then it may be reasonably concluded that the fuel 24 in the storage tank 12 has already separated, and the controller 88 may be configured to notify an operator or provide some other indication of fuel separation. For example, the controller 88 may send an alert to the operator, sound an alarm, or take other action to indicate to the operator that the fuel 24 in the storage tank 12 has separated. In various embodiments, the controller 88 may be configured to shut down the pumps for the dispensing units 18 associated with the fuel tank 12 having separated fuel.

Although in the above description the check to ensure that the fuel 24 in the storage tank 12 has not already separated was conducted using the sensors 90, 92 associated with the test cavity 60 (i.e., the fuel sample in test cavity 60 was tested for separation), it should be recognized that this check may be conducted in other ways. By way of example, sensors similar to sensors 90, 92 (e.g., electrical conductance sensors) may be located adjacent the top surface of the fuel in the storage tank 12 and adjacent the bottom of the storage tank 12 and be configured to indicate separation similar to that described above (not shown). These sensors may be operatively coupled to controller 88 and may allow this check to be done before initiating separation risk testing.

In any event, if it is determined that the fuel 24 in the storage tank 12 has not separated, then the initial temperature of the fuel sample may be determined. In this regard, the controller 88 may receive a signal from temperature sensor 94 (or alternatively from temperature sensor 96) corresponding to the temperature of the fuel sample and store the temperature value into memory. It is noted that in the normal course, this initial temperature corresponds to the temperature of the blended fuel 24 in the storage tank 12.

After determining the initial temperature of the fuel sample, the controller 88 may activate the heat transfer device 78 so as to initiate cooling of the fuel sample in test cavity 60. The heat that is removed from the test cavity 60 is transferred to the heat sink cavity 72 and subsequently carried away by the fuel flowing therethrough (e.g., by the fuel flowing over the finned heat exchanger 120). As the fuel sample is being cooled, the controller 88 may continuously or discretely receive and analyze signals from the first and second sensors 90, 92. If the difference between the measurements of sensors 90, 92 is less than a threshold value then a conclusion may be reasonably drawn that the fuel sample has not separated and cooling of the test cavity 60 may be continued. If, on the other hand, the measurements of sensors 90, 92 differ by more than the threshold value, then a conclusion may be reasonably drawn that the fuel sample has separated into its various phases and the continued cooling of the fuel sample may be terminated. By way of example, a difference formula may be given by $|(S_1-S_2)|/S_1$, where $S_1$ is the value of the measured fluid property from first sensor 90 and $S_2$ is the value of the measured fluid property from second sensor 92. Other difference formulas may be used as well. It should be recognized that the analysis does not have to use the value of the fluid property itself, but may use values (e.g., electrical values, such as voltage, current, etc.) that have a correspondence to the fluid property value. In any event, the threshold value of about 10%-20% may be used and stored in the memory of controller 88.

When the measurements from sensors 90, 92 indicate that the fuel sample in the test cavity 60 has separated, the temperature at which separation occurred (i.e., the saturation temperature) may be noted by receiving a signal from temperature sensor 94 and storing into memory a temperature corresponding to the signal. The risk factor R may then be determined by subtracting the initial temperature of the fuel sample from the saturation temperature in the manner previously discussed. The risk factor R may then be reported to an operator and/or stored in a memory, database, etc. so as to potentially be used for further analysis (e.g., historical analysis).

In one embodiment, the range of risk factors R may be divided into a plurality of categories for identifying the risk that the blended fuel 24 in the storage tank 12 is going to separate. For example, the risk categories of: i) high risk of phase separation; ii) medium risk of phase separation; and iii) low risk of phase separation may be defined. The appropriate category may then be reported to the operator and/or stored in the database. The risk categories may also be color coded with, for example, i) red corresponding to a high risk of phase separation; ii) yellow corresponding to a medium risk of phase separation; and iii) green corresponding to a low risk of phase separation. Other categories may also be defined.

Testing of the fuel 24 in the storage tank 12 may be conducted at regularly scheduled intervals. For example, a test may be conducted on an hourly basis, a daily basis, a weekly basis, a monthly basis, etc. The testing frequency of the fuel in the storage tank 12 may not be regular, but may, for example, increase the longer the fuel 24 is in the storage tank 12. Thus, fuel that has been in the storage tank 12 for a longer period of time will be tested more frequently.

In addition to the above, the data collected over the lifetime of a batch of fuel 24 in the storage tank 12 may be analyzed to determine trends which might be useful in more accurately predicting fuel separation risk. By way of example, a specific storage tank may have a characteristic data curve indicative of, for example, the rate at which water collects within the storage tank. This may vary, for example, by the seasons and other predictable patterns which impact the rate at which water enters the storage tank. By monitoring and analyzing the historical data, such as by extrapolation and other statistical and analytical methodologies, the remaining life of the fuel 24 in the storage tank 12 may be ascertained.

The controller 88 may be capable of further analysis. In this regard, the saturation curve (e.g., see FIG. 2) may be stored in memory in the form of a look up table, for example. When the saturation temperature of the fuel sample is determined in accordance with that described above, the controller 88 may be configured to determine the water percentage of the fuel 24 in the storage tank 12 and report that to the operator and/or store the value in memory, database, etc. This value can also be compared to the saturation water percentage for a fuel at the initial temperature to provide another metric of risk.

In an advantageous aspect, the apparatus and methods described herein provide gas station owners with a greater number of options when it is determined that the fuel in the storage tank is at a high risk of separating. By way of example and not limitation, when notified that fuel in a storage tank is near separation (e.g., high risk), a gas station owner may add more of the blended fuel to the storage tank. This decreases the percentage of water content of the fuel without changing the percent of ethanol of the fuel (i.e., the fuel retains the same E number). Another option is to add more ethanol (without gasoline) to the storage tank. While such a measure would increase the percentage of ethanol of the fuel (e.g., change from E10 to E15), it would also make the fuel safer as it would take a greater amount of water to reach the new saturation point.

In still a further option, upon a gas station owner learning that the fuel in a storage tank is at high risk of separating, the gas station owner may lower the sale price so as to encourage consumption of the fuel prior to its impending separation within the storage tank 12. In other words, the price of the fuel in the storage tank 12 may be set in conjunction with the results of the test so as to ensure that the fuel is sold in a timely manner. Furthermore, the indication that the storage tank is taking on water may warrant an investigation as to the source of the water ingress. For example, the investigation may indicate that certain drainage systems are malfunctioning, or that various seals need replacing.

While the above description is directed to assessing the separation risk of the fuel 24 in the fuel tank 12 of the dispensing system 10, the controller 88 may also be configured to determine a risk of the fuel separating after it has been dispensed to a customer. In this regard, the controller 88 may be coupled to a temperature sensor (not shown) configured to measure the surrounding environmental temperature. In the normal course, once fuel is dispensed into, for example, the gas tank of an automobile, the fuel will come into thermal equilibrium with the environmental temperature. Thus, because the saturation temperature for the fuel has already been determined, the controller 88 may also determine a risk of fuel separation for the customer. By way of example, and similar to that above, a risk factor may be defined as the difference between the environmental temperature $T_e$ and the saturation temperature of the fuel. In equation form, an indication of risk of phase separation to the customer may be defined by $R_{cust}=T_e-T_s$, where $T_s$ is the saturation temperature of the fuel determined in the most recent test, for example.

If the environmental temperature $T_e$ is higher than the temperature of the fuel 24 in the storage tank 12, then according to the saturation curve, the risk factor should increase indicating that the risk of phase separation of the fuel in the customer's gas tank decreases (i.e., it becomes safer). On the other hand, if the environmental temperature $T_e$ is less than the temperature of the fuel 24 in the storage tank 12, then according to the saturation curve, the risk factor should decrease indicating that the risk of phase separation of the fuel in the customer's gas tank increases. Similar to above, various categories may be defined for indicating the risk that the fuel in the customer's gas tank will separate. If the risk to the customer becomes too great, the gas station owner may again have the opportunity to take appropriate measures, including, without limitation, notifying the customer as to the risk, shutting down the affected dispensing units, and/or recommending supplementing the fuel in the customer's gas tank with additional ethanol so as to make the fuel "safer."

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of the general inventive concept.

What is claimed is:

1. A method for handling a blended fuel in a storage tank, comprising:
   obtaining a sample of the blended fuel from the storage tank;
   determining whether the fuel in the storage tank has separated prior to determining a risk that the blended fuel in the storage tank will separate;
   cooling the sample until the sample separates into phases; and
   determining the risk that the blended fuel in the storage tank will separate based on the cooling step.

2. The method of claim 1, wherein obtaining the sample of blended fuel further comprises:
   initiating the flow of fuel into a test cavity; and
   stopping the flow of fuel when a sufficient amount of fuel is disposed in the test cavity.

3. The method of claim 2, further comprising:
   opening an inlet control value controlling the flow of fuel into the test cavity; and
   closing an exit control valve for controlling the flow of fuel out of the test cavity.

4. The method of claim 1, wherein cooling the sample further comprises:
   activating a heat transfer device configured to remove heat from the sample.

5. The method of claim 4, wherein activating the heat transfer device further comprises:
   applying an electrical signal to a thermoelectric device.

6. The method of claim 5, wherein the thermoelectric device is a Peltier device.

7. The method of claim 4, further comprising:
   removing heat from the heat transfer device.

8. A method for handling a blended fuel in a storage tank, comprising:
   obtaining a sample of the blended fuel from the storage tank;
   cooling the sample until the sample separates into phases including activating a heat transfer device configured to remove heat from the sample;
   removing heat from the heat transfer device including circulating fuel so as to remove heat from the heat transfer device; and
   determining a risk that the blended fuel in the storage tank will separate based on the cooling step.

9. The method of claim 8, wherein circulating fuel further comprises:
   circulating fuel through a heat sink cavity in thermal communication with the heat transfer device.

10. The method of claim 1, wherein determining whether the fuel in the storage tank has separated further comprises:
    measuring a fluid property of the sample; and
    comparing the measured fluid property to a value of the fluid property corresponding to the unseparated blended fuel.

11. The method of claim 10, further comprising:
    concluding that the fuel in the storage tank has not separated when the difference between the measured value and the value of the blended fuel is less than a threshold value, or alternatively concluding that the fuel in the storage tank has separated when the difference is greater than the threshold value.

12. The method of claim 1, wherein determining whether the fuel in the storage tank has separated further comprises:
    measuring a fluid property of the fuel in the storage tank; and
    comparing the measured fluid property to a value of the fluid property corresponding to the unseparated blended fuel.

13. The method of claim 12, further comprising:
    concluding that the fuel in the storage tank has not separated when the difference between the measured value and the value of the blended fuel is less than a threshold value, or alternatively concluding that the fuel in the storage tank has separated when the difference is greater than the threshold value.

14. The method of claim 1, further comprising:
    determining whether the sample has separated as the sample is being cooled.

15. The method of claim 14, wherein determining whether the sample has separated further comprises:
measuring a fluid property of the sample at a first location;
measuring the fluid property of the sample at a second location; and
comparing the measured fluid property values.

16. The method of claim 15, further comprising:
concluding that the sample has not separated when the difference between the measured values is less than a threshold value, or alternatively concluding that the sample has separated when the difference is greater than the threshold value.

17. The method of claim 1, further comprising:
determining the temperature of the fuel in the storage tank.

18. The method of claim 17, wherein determining the temperature of the fuel in the storage tank further comprises:
determining the initial temperature of the sample prior to cooling the sample.

19. The method of claim 1, further comprising:
determining the temperature of the sample when the sample separates.

20. The method of claim 1, wherein determining the risk that the fuel in the storage tank will separate further comprises:
defining a risk factor.

21. The method of claim 20, wherein the risk factor is defined by a difference between the temperature of the fuel in the storage tank and the temperature of the sample when the sample separates.

22. The method of claim 1, further comprising:
sending an alert to an operator when the risk of phase separation reaches a threshold criteria.

23. The method of claim 1, further comprising:
determining the water content of the fuel in the storage tank.

24. The method of claim 23, wherein determining the water content of the fuel in the storage tank further comprises:
determining the temperature of the sample when the sample separates; and
determining the water content of the sample using the saturation temperature.

25. The method of claim 24, wherein determining the water content using the saturation temperature further comprises:
using a look up table that provides saturation curve information.

26. The method of claim 1, further comprising:
determining the risk that the fuel in the gas tank of a customer will separate.

27. The method of claim 26, wherein determining the risk that fuel in the customer's gas tank will separate further comprises:
determining the temperature of the sample when the sample separates;
determining an environmental temperature; and
defining a risk factor by a difference between the environmental temperature and the temperature of the sample when the sample separates.

28. A method for handling a blended fuel in a storage tank, comprising:
obtaining a sample of the blended fuel from the storage tank;
determining whether the fuel in the storage tank has separated prior to determining the temperature of the sample when the sample separates;
determining the temperature of the fuel in the storage tank;
cooling the sample until the sample separates into phases;
determining whether the sample has separated as the sample is being cooled;
determining the temperature of the sample when the sample separates; and
determining a risk that the fuel in the storage tank will separate based on a difference between the temperature of the fuel in the storage tank and the temperature of the sample when it separates.

29. An apparatus for assessing the risk of phase separation of a blended fuel, comprising:
a test cavity for holding a sample of a blended fuel from a storage tank;
a heat transfer device for cooling the sample in the test cavity;
at least one sensor for indicating when the sample in the test cavity has separated; and
a controller operatively connected to the at least one sensor, the controller configured to determine whether the fuel in the storage tank has separated and, subsequently, to determine the risk of phase separation of the blended fuel within the storage tank based on when the sample in the test cavity has separated and send an alert to an operator of the risk of phase separation.

30. The apparatus of claim 29, further comprising a temperature sensor associated with the test cavity.

31. The apparatus of claim 29, further comprising:
a first control valve associated with the inlet to the test cavity; and
a second control valve associated with the outlet of the test cavity.

32. The apparatus of claim 29,
wherein the controller is operatively coupled to the test cavity and the heat transfer device.

33. The apparatus of claim 29, wherein the at least one sensor includes a sensor adjacent a top of the test cavity and a sensor adjacent a bottom of the test cavity.

34. The apparatus of claim 29, wherein the at least one sensor is configured to measure the electrical conductivity of the fuel.

35. The apparatus of claim 29, wherein the heat transfer device is a Peltier device.

36. An apparatus for assessing the risk of phase separation of a blended fuel, comprising:
a test cavity for holding a sample of a blended fuel from a storage tank;
a heat transfer device for cooling the sample in the test cavity;
a heat sink cavity configured to circulate fuel for removing heat from the heat transfer device;
at least one sensor for indicating when the sample in the test cavity has separated; and
a controller operatively connected to the at least one sensor, the controller configured to determine the risk of phase separation of the blended fuel within the storage tank based on when the sample in the test cavity has separated and send an alert to an operator of the risk of phase separation.

37. The apparatus of claim 36, further comprising:
a temperature sensor associated with the heat sink cavity.

38. A fuel dispensing system, comprising:
a storage tank containing a blended fuel;
a dispensing unit configured to dispense the blended fuel;
a conduit line between the storage tank and the dispensing unit for transporting the fuel; and a phase separation monitoring device for providing information about the fuel in the storage tank relative to separation of the fuel, the phase separation monitoring device including:
a test cavity for holding a sample of a blended fuel from the storage tank;
a heat transfer device for cooling the sample in the test cavity;
at least one sensor for indicating when the sample in the test cavity has separated; and
a controller operatively connected to the at least one sensor, the controller configured to determine whether the fuel in the storage tank has separated and, subsequently, to determine the risk of phase separation of the blended fuel within the storage tank based on when the sample in the test cavity has separated and send an alert to an operator of the risk of phase separation.

* * * * *